US008198293B2

(12) United States Patent
Chia

(10) Patent No.: US 8,198,293 B2
(45) Date of Patent: Jun. 12, 2012

(54) OXYMATRINE COMPOSITIONS AND RELATED METHODS FOR TREATING AND PREVENTING CHRONIC INFECTIOUS DISEASES

(76) Inventor: John K. S. Chia, Lomita, CA (US)

( * ) Notice: Subject to any disclaimer, the term of this patent is extended or adjusted under 35 U.S.C. 154(b) by 0 days.

(21) Appl. No.: 12/509,373

(22) Filed: Jul. 24, 2009

(65) Prior Publication Data

US 2010/0022575 A1 Jan. 28, 2010

Related U.S. Application Data

(60) Provisional application No. 61/083,471, filed on Jul. 24, 2008.

(51) Int. Cl.
*A61K 31/44* (2006.01)
*A01N 43/40* (2006.01)
*A01N 43/42* (2006.01)

(52) U.S. Cl. ......................... 514/285; 514/277; 514/284

(58) Field of Classification Search .................. 514/285
See application file for complete search history.

(56) References Cited

U.S. PATENT DOCUMENTS

2005/0096369 A1* 5/2005 Hoang .......................... 514/400

FOREIGN PATENT DOCUMENTS

WO 2008/102997 A 8/2008

OTHER PUBLICATIONS

Dong et al. (Effects of oxymatrine on the serum levels of T helper cell 1 and 2 cytokines and the expression of the S gene in hepatitis B virus S gene transgenic mice: a study on the anti-hepatitis B virus mechanism of oxymatrine), J Gastroenterol Hepatol Dec. 2002; 17 (12): 1299-306.*

Illinois State Board of Education and Illinois Department of Public Health (Revised Edition 2003), Management of Chronic Infectious Diseases in Schoolchildren, printed pp. 1-39.*

Maillefert et al. (Rheumatic disorders developed after hepatitis B vaccination), Rheumatology 1999; 38 978-983.*

Lee et al. “Executive summary of Report: Hepatitis B vaccine and putative associations with (a) Arthritis (b) Chronic Fatigue Syndrome.” London School of Hygiene and Topical Medicine, Nov. 2005.

Reeves et al. “Identification of ambiguities in the 1994 chronic fatigue syndrome research case definition and recommendations for resolution.” BMC Health Services Research 2003, 3:25.

Jiang Y. et al. “Th1 and Th2 immune response in chronic hepatitis B patients during a long-term treatment with adefovir dipivoxil.” Mediators of Inflammation. vol. 2010, Article ID 143026, 10 pages, 2010.

Shirakawa H. et al. “Pretreatment prediction of virological response to peginterferon plus ribavirin therapy in chronic hepatitis C patients using viral and host factors.” Hepatology 48:1753-60, 2008.

Clerici M. et al. Cytokine dysregulation in invasive cervical carcinoma and other human neoplasias: time to consider the TH1/TH2 paradigm. Journal of the National Cancer Institute 90:261-263, 1998.

Surcel H.-M. et al. Th1/Th2 profiles in tuberculosis, based on the proliferation and cytokine response of blood lymphocytes to mycobacterial antigens. Immunology 81:171-176, 1994.

Hepatitis B vaccination and chronic fatigue syndrome, Committee Reports, WER Jan. 13, 2006).

Database WPI Week 200864, “Medicine for treating herpes zoster, includes common cnidium fruit, arsenic sulfide, dragon’s blood, *Radix sophorae*, and pepper.” Jun. 11, 2008 (abstract).

Database WPI Week 200863, “Use total alkaloid in *Sophora alopecuroids* in preparing medicine for treating herpes zoster in short duration of time.” Feb. 27, 2008 (abstract).

Wu et al. “experimental studies of oxymatrine and its mechanisms of action in hepatitis B and C viral infections.” Chinese Journal of Digestive Diseases, vol. 5, No. 1, 2004, pp. 12-16.

* cited by examiner

*Primary Examiner* — Sreeni Padmanabhan
*Assistant Examiner* — Timothy E Betton
(74) *Attorney, Agent, or Firm* — K&L Gates LLP; Louis C. Cullman; Michelle Glasky Bergman

(57) ABSTRACT

Compositions and methods for treating chronic infectious diseases using substantially pure oxymatrine or pharmaceutically acceptable salts or esters thereof are disclosed. In one embodiment described herein, the chronic infectious disease is chronic fatigue syndrome. Further described are compositions having an anti-infective amount of substantially pure oxymatrine or pharmaceutically acceptable salts or esters thereof.

11 Claims, 5 Drawing Sheets

OXYMATRINE COMPOSITIONS AND RELATED METHODS FOR TREATING AND PREVENTING CHRONIC INFECTIOUS DISEASES

FIELD OF THE INVENTION

Described herein are compositions and methods for treating chronic infectious diseases, specifically oxymatrine compositions and related methods of use. More specifically, described herein are methods of treating chronic fatigue syndrome using oxymatrine compositions.

BACKGROUND

A proper immune response is paramount in controlling intracellular infections. Activation of T helper 1 lymphocyte (Th1) response is usually associated with eradication of the infectious agents during acute infection. A shift to a T helper 2 (Th2) profile is, however, associated with persistent infection, as documented in patients with lepromatous leprosy, disseminated tuberculosis, and leishmaniasis. Without improving the T cell responses, traditional antimicrobial treatments of these chronic infections, if available, are usually prolonged, if not life-long in some cases.

Matrine and oxymatrine are two of the natural compounds isolated from the root of the herb *Sophora flavescens*. These two compounds have shown antiviral activity in vitro and in vivo by scientists and clinicians. In vitro experiments have demonstrated growth inhibition of coxsackievirus B and echoviruses in cell cultures, although the mechanism has not been defined (See Chen S X, et al., *Effect of Sophora flavescens on cultured beating myocardial cells of coxsackie B*3 *virus infected newborn rat*, Chinese Journal of Infectious Diseases, 2000; 14(2), 137-140 and Chen Ting Ting, et al. Ku shen, *Total alkaloid's protective effects on counteracting Coxsackievirus B infected HeLa cells*, Chinese journal of experimental clinical immunology. 197; 9, 18-21).

Administration of oxymatrine to transgenic mice chronically infected with hepatitis B virus demonstrated a shift in T cell response, and therefore, the cytokine profile from Th2 to Th1, as compared to placebo-treated animals. Specifically, the levels of gamma interferon and interleukin-2 increased more than three-fold, whereas the levels of interleukin-4 and interleukin-10 decreased more than three-fold. No effect on the hepatitis B viremia, mRNA and protein levels was demonstrated in these experiments (See Yuhong et al., *Antihepatitis B virus mechanism of oxymatrine* J. Gastro. Hepatol. 2002; 17, 1299-1306).

Clinically, intravenous matrine has been used to treat viral myocarditis in countries such as China. In one placebo-controlled study, more than 90% of the patients with chronic Coxsackievirus B myocarditis had an improvement of cardiac function, increase in lymphocyte number and function, and loss of viral markers when treated with intravenous matrine, as compared to 0% in the placebo-treated group (Chen et al., *Therapeutic effect of kangke injection on viral myocarditis and its anticoxsackie virus mechanism*, Chinese Journal of Integrated Traditional and Western Medicine 1997; 17(4), 207-209).

Oxymatrine is an oral agent used for the treatment of chronic hepatitis B. The overall cure rate is about 40% after one year of treatment, comparable to that of interferon-α injection (Xie Ning Wu et al., *Experimental studies of oxymatrine and its mechanisms of action in hepatitis B and C viral infections*, Chinese Journal of Digestive Diseases 2004; 5(1), 12-16).

Chronic fatigue syndrome (CFS) remains an elusive disease even after more than two decades of research (Reeves W C et al., *Identification of ambiguities in the* 1994 *chronic fatigue syndrome research case definition and recommendations for resolution*, BMC Health Serv Res. 2003; 3, 25-29). A severe flu-like illness that occurrs in the majority of CFS cases, followed by persistent illness and fatigue, suggest an infectious etiology triggering and the possibly of perpetuating this syndrome. In small subsets of patients, Epstein-Barr virus (EBV), Cytomegalovirus (CMV), HHV-6, Parvovirus B19, Brucella, Toxoplasma, *Coxiella burnetii*, Russ river virus and *Chlamydia pneumoniae* have been reported to cause prolonged fatigue, fevers and many other symptoms of CFS (Chia, J. K., *The role of enterovirus in chronic fatigue syndrome*, J. Clin. Path. 2005; 58, 1126-1132).

Currently, there are likely more than 7.5 million CFS patients in the United States alone. Initial analysis of 200 CFS patients suggests that CFS may have a number of potentially treatable infectious etiologies as previously reported, and enteroviruses accounted for more than half of the cases, as documented by elevated neutralizing antibody titers and positive enterovirus RNA in the peripheral blood leukocytes.

Since most CFS patients have persistent or intermittent gastrointestinal (GI) symptoms, the presence of viral capsid protein 1 (VP1), enterovirus (EV) RNA and culturable virus in the stomach biopsy specimens of patients with CFS was evaluated. It was found that 82% (135/165) of CFS biopsies stained positive for VP1 within parietal cells, whereas 20% (7/34) of the controls stained positive for VP1 within parietal cells ($p \leqq 0.001$). CMV mAb failed to stain any of the biopsy specimens. Biopsies taken from six patients both at the onset of the CFS/abdominal symptoms and 2-8 years later showed positive staining in the paired specimens. EV RNA was detected in 37% (9/24) paraffin-embedded CFS biopsy samples; 4.8% (1/21) of controls had detectable EV RNA ($p<0.01$); 33% (1/3) of patients had detectable EV RNA from two samples taken four years apart; and more than ten stomach biopsy samples showed transient growth of non-cytopathic EV. These findings suggest that persistent EV infection is present in a high percentage of CFS patients and may be the etiologic agent responsible for the profound symptomatology.

Varying immunologic abnormalities have been long described in patients with CFS. A bias toward Th2 response has been demonstrated. In overnight cultures with or without prior polyclonal activation, a significantly higher percentage of CD8+T lymphocytes from CFS patients produced interleukin-4, interleukin-10 and gamma interferon, but not interleukin-2. When compared to control subjects, the difference was not accountable by other measurements of allergic response.

SUMMARY

Disclosed are compositions and methods for treating chronic infectious diseases. Specifically, the present description is directed to oxymatrine compositions and related methods of use. More specifically, described are methods of treating chronic fatigue syndrome using oxymatrine compositions.

In one embodiment, described herein are methods for treating a human patient suffering from at least one chronic infectious disease by administering an anti-infective amount of substantially pure oxymatrine or pharmaceutically acceptable salts or esters thereof. The oxymatrine composition can be a solution, tablet, capsule, suppository or inhalable dosage form. The oxymatrine composition may be administered parenterally, orally or by any other means appropriate for the particular dosage form.

In another embodiment, the chronic infectious diseases to be treated or prevented include chronic fatigue syndrome, myalgic encephalomyelitis, shingles, mononucleosis, and chronic enterovirus infections.

The methods, in other embodiments, further include the step of diagnosing the chronic infectious disease using a gastrointestinal biopsy before the administering step. The gastrointestinal biopsy, for example can be a stomach biopsy, a colon biopsy or the like. In another embodiment, the gastrointestinal biopsy is stained.

The substantially pure oxymatrine may be administered one to three times per day in an amount between about 10 mg and about 1000 mg. Although less frequent administrations may be appropriate in certain patients, the attending physician may dictate less frequent administrations. Examples of less frequent administrations may include once every other day, once weekly, once monthly, and the like. Moreover, while the present disclosure is primarily directed at therapeutic doses and regimens, maintenance doses and administration schedules are also contemplated.

In another embodiment, the substantially pure oxymatrine is an immunostimulatory composition comprising substantially pure oxymatrine or pharmaceutically acceptable salts and esters thereof and other pharmaceutically acceptable excipients. In yet another embodiment the substantially pure oxymatrine is an immunostimulatory composition consisting essentially of substantially pure oxymatrine or pharmaceutically acceptable salts and esters thereof and other pharmaceutically acceptable excipients.

DETAILED DESCRIPTION

Figure 1:
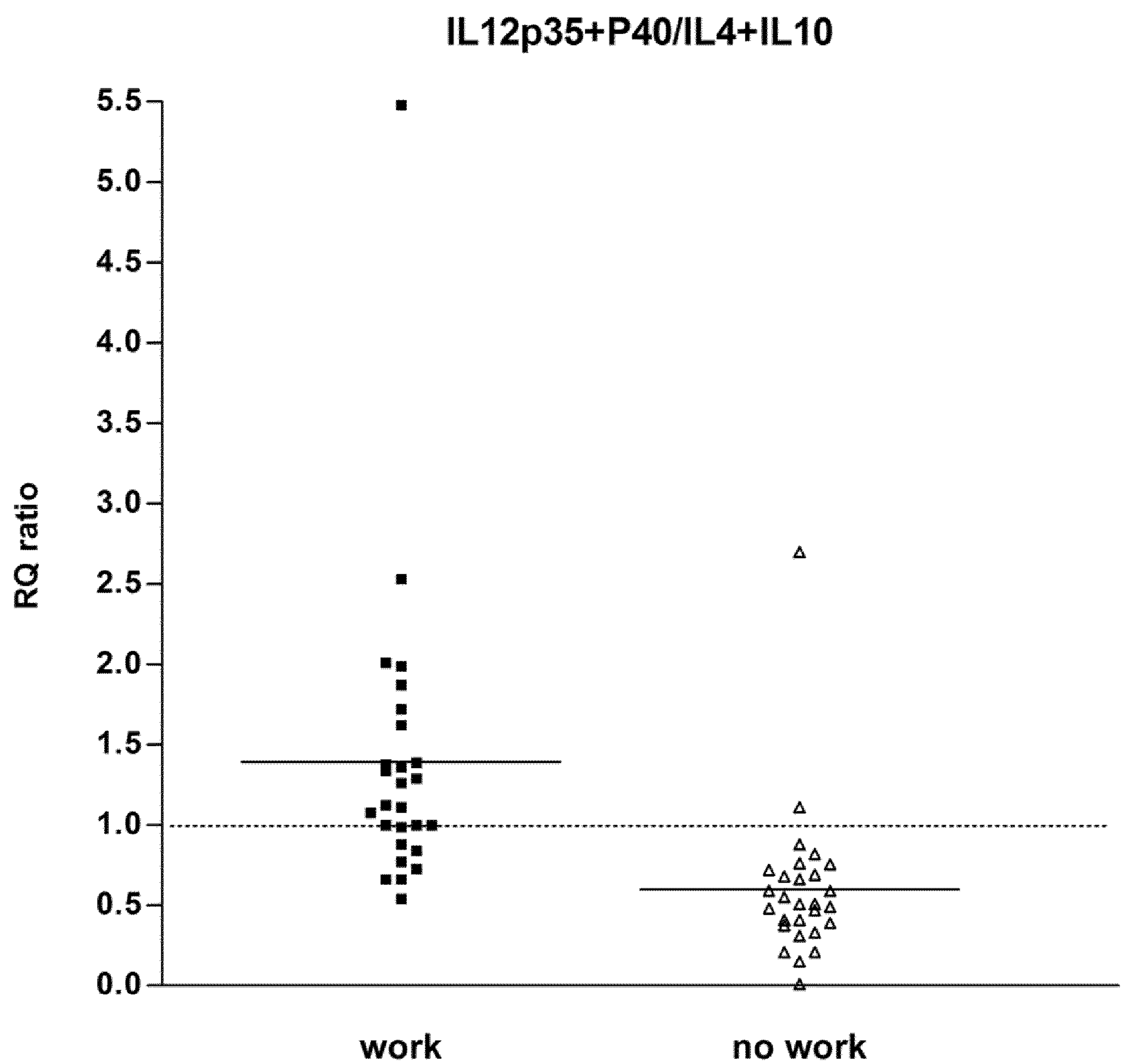
FIG. 1 graphically illustrates the comparison of Th1/Th2 (interleukin-12p35+P40/interleukin-4+ interleukin-10, RQ is the gene expression ratio) gene expression of patients who are functional (able to work) versus totally disability (not able to work). The difference therein is statistically significant ($p<0.01$, pair t test).

Disclosed herein are methods and compositions for treating chronic and acute infectious diseases using substantially pure oxymatrine and pharmaceutically acceptable salts and esters thereof. In some embodiments, the oxymatrine is administered in an anti-infective amount. "Anti-infective" is an amount of substantially pure oxymatrine that overcomes an infection or substantially relieves the symptoms thereof, or causes the infection to enter remission.

The term "substantially pure" refers to oxymatrine made using pharmaceutical manufacturing processes equivalent to "Good Manufacturing Procedures" described by the United States Food and Drug Administration (FDA), not crude herbal extracts or powders. Thus the term "substantially pure" distinguishes the compositions described herein from crude herbal extracts or naturally occurring botanical products that have not been subjected to rigorous methods of purification and extraction. The oxymatrine compositions described herein are at least 90% pure oxymatrine, preferably 95% percent pure, even more preferably 99% percent pure oxymatrine. In other embodiments, the oxymatrine is greater than 99% pure.

As used herein, "pharmaceutically acceptable salt" refers to any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt. Further, pharmaceutically acceptable salt refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Esters of oxymatrine are also contemplated, particularly ester prodrugs. An ester may be derived from a carboxylic acid of oxymatrine, or an ester may be derived from a carboxylic acid functional group substituted on another part of the molecule. While not intending to be limiting, an ester may be an alkyl ester, an aryl ester, or a heteroaryl ester.

An ester prodrug is converted to a therapeutically active oxymatrine after administration, and the term should be interpreted as broadly herein as is generally understood in the art. While not intending to limit the scope of the present description, conversion may occur by hydrolysis of an ester group. Generally, but not necessarily, a prodrug is inactive or less active than the therapeutically active oxymatrine to which it is converted after administration.

The methods described herein are used for treating at least one chronic infectious disease, the methods comprising administering to a human patient suffering from the at least one chronic infectious disease an anti-infective amount of substantially pure oxymatrine or a pharmaceutically acceptable salt or ester thereof; and treating the at least one chronic infectious disease.

The methods, in other embodiments, further include the step of diagnosing the chronic infectious disease using a gastrointestinal biopsy before the administering step. The gastrointestinal biopsy, for example can be a stomach biopsy, a colon biopsy or the like. In another embodiment, the gastrointestinal biopsy is stained using convention staining methods known in the art.

The compositions described herein can be used to treat or prevent at least one chronic infectious disease, for example, chronic fatigue syndrome, myalgic encephalomyelitis, shingles, mononucleosis, chronic enterovirus infections and the like.

Oxymatrine is one of two major alkaloid components found in sophora roots. They are obtained primarily from *Sophora japonica* (*kushen*), but also from *Sophora subprostrata* (*shandougen*), and from the above ground portion of *Sophora alopecuroides*. Oxymatrine was first isolated and identified in 1958 and is a unique tetracyclo-quinolizindine alkaloid(s) found only in *Sophora* species to date. The chemical structure for oxymatrine is depicted in Formula 1. Methods for the isolation and purification of oxymatrine are well known in the art.

Formula 1

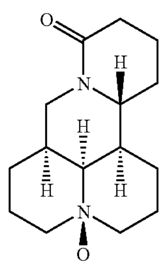

The compositions described herein may be administered at pharmaceutically effective, anti-infective dosages. Such dosages are normally the minimum dose necessary to achieve the desired therapeutic effect; in the treatment of enterovirus infection, for example, this amount would be roughly that necessary to reduce the symptoms of the enterovirus infection to tolerable levels.

In one embodiment, therapeutic doses of the substantially pure oxymatrine are in the range 1-1000 mg/day; more preferably in the range 10 to 500 mg/day. In another example embodiment, the oxymatrine may be present in a composition in a range of about 0.5 mg/kg/day to about 100 mg/kg/day. However, the actual amount of oxymatrine to be administered in any given case will be determined by a physician taking into account the relevant circumstances, such as the severity of the infection, the age and weight of the patient, the patient's general physical condition, and the route of administration.

In one embodiment, therapeutic doses of the substantially pure oxymatrine are administered twice daily at a dose of between about 5 mg and about 500 mg per administration; between about 10 mg and about 450 mg per administration; between about 50 mg and about 375 mg per administration; between about 100 mg and about 250 mg per administration; between about 150 mg and about 225 mg per administration; or between about 175 mg and about 200 mg per administration.

Similar dosage ranges are also suitable as maintenance doses as determined by the attending physician. Essentially, a patient can be treated with progressively smaller doses until an optimum minimal dose is found that suppresses reoccurrences of symptoms. Thereafter, dose frequency can be titrated to determine the minimum dosage schedule necessary to prevent disease reoccurrence at the minimum dose.

In other embodiments, the patient is administered a composition orally in any acceptable form, such as a tablet, liquid, capsule, powder and the like. However, other routes may be desirable or necessary. Such other routes may include, without exception, transdermal, parenteral, subcutaneous, intranasal, intrathecal, intramuscular, intravenous, and intrarectal modes of delivery. Additionally, formulations may be designed to delay release of the active compound over a given period of time, or to carefully control the amount of oxymatrine released at a given time during the course of therapy.

In another embodiment, provided are pharmaceutical compositions including therapeutic doses of the substantially pure oxymatrine in a pharmaceutically acceptable carrier or excipient. The phrase "pharmaceutically acceptable" means the carrier, dilutent or excipient must be compatible with the other ingredients of the formulation and not deleterious to the recipient thereof.

Pharmaceutical compositions can be used in the form of a solid, a solution, an emulsion, a dispersion, a micelle, a liposome, and the like, wherein the resulting composition contains therapeutic doses of the substantially pure oxymatrine as described herein, as an active ingredient, in admixture with an organic or inorganic carrier or excipient suitable for enteral or parenteral applications. Therapeutic doses of the substantially pure oxymatrine may be combined, for example, with the usual non-toxic, pharmaceutically acceptable excipients for tablets, pellets, capsules, suppositories, solutions, emulsions, suspensions, and any other form suitable for use. The excipients which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers or excipients suitable for use in manufacturing preparations, in solid, semisolid, or liquid form. In addition, auxiliary, stabilizing, thickening and coloring agents and perfumes may be used. Therapeutic, anti-infective doses of the substantially pure oxymatrine described herein are included in pharmaceutical compositions in an amount sufficient to produce the desired effect upon the infective condition.

Pharmaceutical compositions may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing therapeutic doses of the substantially pure oxymatrine as described herein in admixture with non-toxic pharmaceutically acceptable excipients may also be manufactured by known methods.

The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some embodiments, formulations for oral use may be in the form of hard gelatin capsules wherein the therapeutic doses of the substantially pure oxymatrine are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may also be in the form of a sterile injectable suspension. Suspensions may be formulated according to known methods using suitable dispersing or wetting agents and suspending agents. The sterile injectable preparations may also be sterile injectable solutions or suspensions in a non-toxic parenterally-acceptable diluent or solvent, for example, as a solution in 1,3-butanediol. Sterile, fixed oils are conventionally employed as a solvent or suspending medium. For this purpose, any bland fixed oil may be employed including synthetic mono- or diglycerides, fatty acids, naturally occurring vegetable oils, for example, sesame oil, coconut oil, peanut oil, cottonseed oil, etc., or synthetic fatty vehicles like ethyl oleate or the like. Buffers, preservatives, antioxidants, and the like can be incorporated as required.

Compositions described herein may also be administered in the form of suppositories for rectal administration. These compositions may be prepared by mixing the compounds with a suitable non-irritating excipient, such as cocoa butter, synthetic glyceride esters of polyethylene glycols, which are solid at ordinary temperatures, but liquefy and/or dissolve in the rectal cavity to release the therapeutic dose of the substantially pure oxymatrine.

Example 1

Oxymatrine Clinical Study

An open-label, controlled study was conducted on patients who fulfilled the international criteria for myalgic encephalomyelitis (ME)/chronic fatigue syndrome (CFS) and had virological evidence of enterovirus infection. The evidence included significantly positive antibody tests for one or more of eleven enteroviruses (EV), positive enterovirus RNA in the whole blood and/or positive enterovirus staining of stomach biopsies.

One hundred patients took oxymatrine at dose of 200-300 mg twice a day with or without food for a minimum of three months. Patients who could not complete the course due to side effects or intolerance were considered as failures (intent-to-treat analysis). Of the first group, 52% (52/100) responded to oxymatrine, as compared to 6% (7/114) of the control groups ($p<0.000001$, $x^2$ test). Of the next 104 patients, 52% responded to treatment. Age, sex and duration of illness did not correlate with response. Fifty-three percent (57/107) of patients with elevated coxsackie virus B (CVB) and echovirus (Ech) antibody responded to therapy and 50% (49/97) of patients with non-typeable EV infections improved (NS, $x^2$ test). Fifty-two percent (47/91) of patients with positive EV protein in stomach biopsies responded, whereas 56% (5/9) of patients with negative biopsies responded (NS, $x^2$ test).

Relapse of symptoms was common after discontinuing oxymatrine. Fifty-nine percent (19/32) of patients (4 male, 15 female) relapsed within two days to one month after discontinuation of oxymatrine. Eighty-seven percent (13/15) of patients who relapsed responded to restart of oxymatrine. Subsequent responders were continued on oxymatrine beyond six months.

A small percentage (2/204) of patients had transient increase in potassium, which returned to normal without specific treatment. A small percentage of patients (2/204) had elevated blood pressure that prompted discontinuation of therapy. There were no significant changes of other chemistry parameters and complete blood counts (CBC) as compared to baseline values. Transient, moderate increase in pre-existing symptoms were reported by more than 50% of the patients but most patients continued to take the herbs at the same or reduced dose. Twenty patients (10%) stopped oxymatrine within the first eight weeks due to intolerable side effects. No serious complications occurred during therapy. Table 1 lists side effects observed in 176 patients having taken oxymatrine.

TABLE 1

| Type of symptoms | Number of patients (n) | % of total patients |
|---|---|---|
| Increased myalgia | 50 | 30 |
| Increased headache | 14 | 8 |
| Increased abdominal pain | 10 | 6 |
| Increased nausea | 10 | 6 |
| Increased diarrhea | 7 | 4 |
| Increased fatigue | 6 | 4 |
| Increased palpitation, chest pain | 5 | 3 |
| Increased sinus congestion | 5 | 3 |
| Fevers | 4 | 2 |
| Increased bladder symptoms | 3 | 2 |
| Increased dizziness | 3 | 2 |
| Increased insomnia | 3 | 1 |
| Weight gain | 2 | 1 |
| Increase in blood pressure | 2 | 1 |
| Increase in edema | 2 | 1 |
| Increased polyarthralgia | 2 | 1 |
| New rashes | 1 | <1 |
| Diffuse rashes | 1 | <1 |
| Seizure (petit mal) | 1 | <1 |
| Dry eyes and mouth | 2 | 1 |
| Inflammation of skin lesion | 2 | 1 |
| Herpes simplex virus outbreak after discontinuation | 2 | 1 |

Most of the patients tolerated oxymatrine well except for variable increase of pre-existing symptoms, such as headache, myalgia, abdominal pain, nausea, insomnia and at times, fevers during the first 1-2 days of taking the maximal doses. The increase in symptoms typically lasted a few days to several weeks and was much better tolerated when the dose of medication was increased gradually over a 2-3 week period or longer. Few patients experienced an increase in appetite and slight weight gain. One of the 176 patients developed self-limited petit mal seizures, which did not recur after stopping the product. Two patients had an increase in blood pressure while on therapy, which resolved with anti-hypertensive medication or resolved after cessation of oxymatrine.

In one patient, a severe increase in febrile response and marked worsening of symptoms toward the end of the three months of medication administration was associated with lasting remission. The increase in immune response is similar to immune reconstitution reported with other infections.

Example 2

Treatment of Chronic Fatigue

A 59 year-old Japanese-American male with episodes of diarrhea while traveling to Tonga developed severe respiratory infection soon thereafter. The symptoms consisted of fevers to 105° F., night sweats, diffuse myalgia, tachycardia, fatigue, sinus congestion and cough, and unresponsiveness to antibiotics. The patient developed profound fatigue thereafter and went on total disability three months after the onset of symptoms. Initial Coxsackie B virus (CBV) 3, CVB4 and echovirus 9 antibody titers were 1:320, 1:160, 1:80 (normal <1:10), respectively.

The patient could not work for the next 18 months. He was started on oxymatrine at 300 mg twice a day (bid). After taking oxymatrine for two months, he was able to take short walks, but still exhausted after one hour of activity requiring five hour naps. At the end of three months of therapy, he started having fevers of 104-105° F. for several days with marked decrease in diffuse myalgia. Three months after the patient finished taking the medication, he went back to full-time work. During therapy, laboratory studies including CBC and complete chemistry panel were normal except mildly elevated calcium levels, which resolved after stopping hydrochlorothiazide, which the patient also started about the same time for hypertension. CVB3, CVB4 and echovirus antibody three months after therapy were 1:160, 1:160 and 1:20, respectively. The patient had not relapsed for at least one year after therapy.

Example 3

Treatment of Chronic Fatigue

A 45 year white male who had recurrent episodes of debilitating fatigue became totally incapacitated after approximately 17 years. The patient was treated with a combination of alpha and gamma interferon for six weeks with acceptable results. He went into remission but relapsed nine months later after developing a minor upper respiratory infection. He improved minimally after several months of bed rest, but was barely able to work six hours per day. He had brain fog, myalgia (7/10 pain) and was barely able to walk even 1-2 blocks. A stomach biopsy showed enteroviral protein by immunochemical staining consistent with chronic enterovirus infection. Antibodies for 11 of the enteroviruses showed no significant elevation of titers.

Three days after taking oxymatrine at a dose of 300 mg bid, the myalgia intensified (10/10 pain), especially one hour after taking the pills. One week after starting oxymatrine, routine laboratory tests including CBC, chemistry panel and creatine phosphokinase (CPK) were normal. He continued having significant fatigue and myalgia for the next three weeks, but the symptoms resolved one week after stopping the medication. Mild increase in myalgia recurred three days after resuming oxymatrine, but resolved after continuing the medication for the next two weeks. The patient felt well at the end of three months with minimal discomfort in a few muscle groups.

Severe myalgia recurred after resuming vigorous exercise for three weeks while taking oxymatrine. He had to stop exercise for the two months allowing cessation of myalgia. After taking oxymatrine for six months, the patient felt well. Over the next six months after stopping the medication, the patient continuously performed heavy physical activities without significant difficulty. After developing another episode of upper respiratory symptoms, his symptoms relapsed. He has resumed oxymatrine but experienced increasing myalgia as the fatigue improved.

Example 4

Treatment of Chronic Fatigue

A 42 year-old Vietnamese female with a known history of frequent respiratory infections and vasovagal syncope developed respiratory infection, which was followed by bedridden fatigue. Enteroviral protein was detected in the stomach biopsy consistent with chronic enterovirus infection. Approximately five months later, she was started on oxymatrine, which she tolerated well without any adverse reactions. She returned to full-time work after taking the medication for six weeks. After vigorous exercise, she would still have relapses of bedridden fatigue for one day but continued to work 10-12 hours per day for the next 12 months, walking two miles per day. Laboratory tests were normal while on therapy.

Example 5

Treatment of Chronic Fatigue

A 35 year-old white female developed debilitating fatigue, sore throat, oral ulcers, vertigo, headaches and cognitive dysfunction two months after having a flu-like illness. She did not respond to antibiotics or to valacyclovir, and her condition continued for the next four years. Stomach biopsy showed extensive enterovirus protein by immunochemical staining. Approximately four years later, the patient started taking oxymatrine. After an initial increase of gastrointestinal symptoms for the first two weeks, the patient tolerated 500 mg per day of oxymatrine.

Two months after taking the medication, the patient had severe diffuse ulcerations of the mouth mucosa, increasing headache, sinus congestion and severe myalgia. The symptoms continued for two weeks and resolved after stopping oxymatrine. Three months later, she only had mild symptoms and was able to return to part-time work and regular exercise. She continued to improve for 12 months after taking the medication.

Example 6

Staining of Stomach Biopsy

Figure 2:
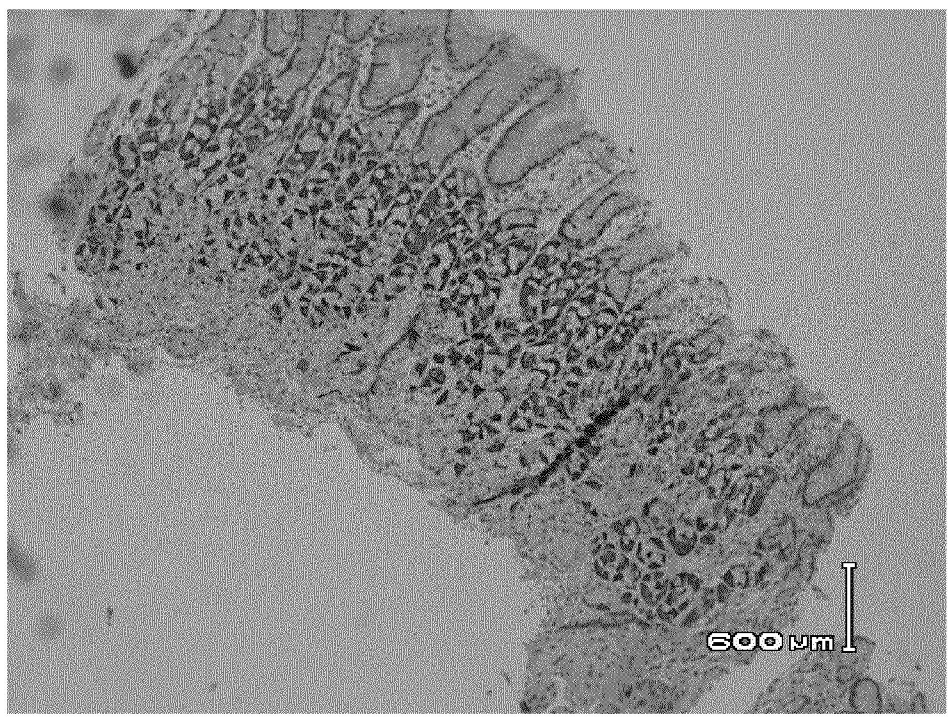
FIG. 2 illustrates the infected human stomach (biopsy of case 5 stained with 5D8/1) before treatment with oxymatrine.
Figure 3:
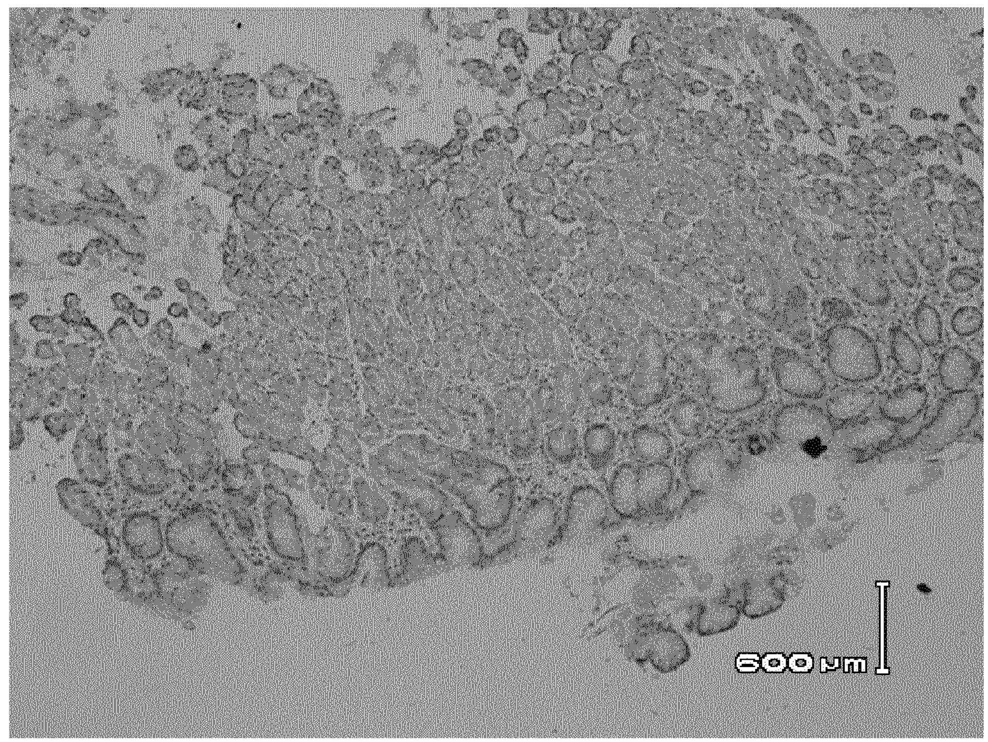
FIG. 3 illustrates the stomach biopsy of case 5 stained with 5 D8/1 after taking oxymatrine for 6 months.

FIG. 2 illustrates immunoperoxidase staining for enterovirus protein in a stomach biopsy before oxymatrine therapy for one patient. FIG. 3 illustrates immunoperoxidase staining of a stomach biopsy for enterovirus after initiation of oxymatrine therapy for the same patient, showing significant reduction in viral protein by staining with enterovirus-specific monoclonal antibody (5 D8/1). The decrease in viral protein correlated with significant symptomatic improvement.

Example 7

Gene Expression Study Results

Figure 4:
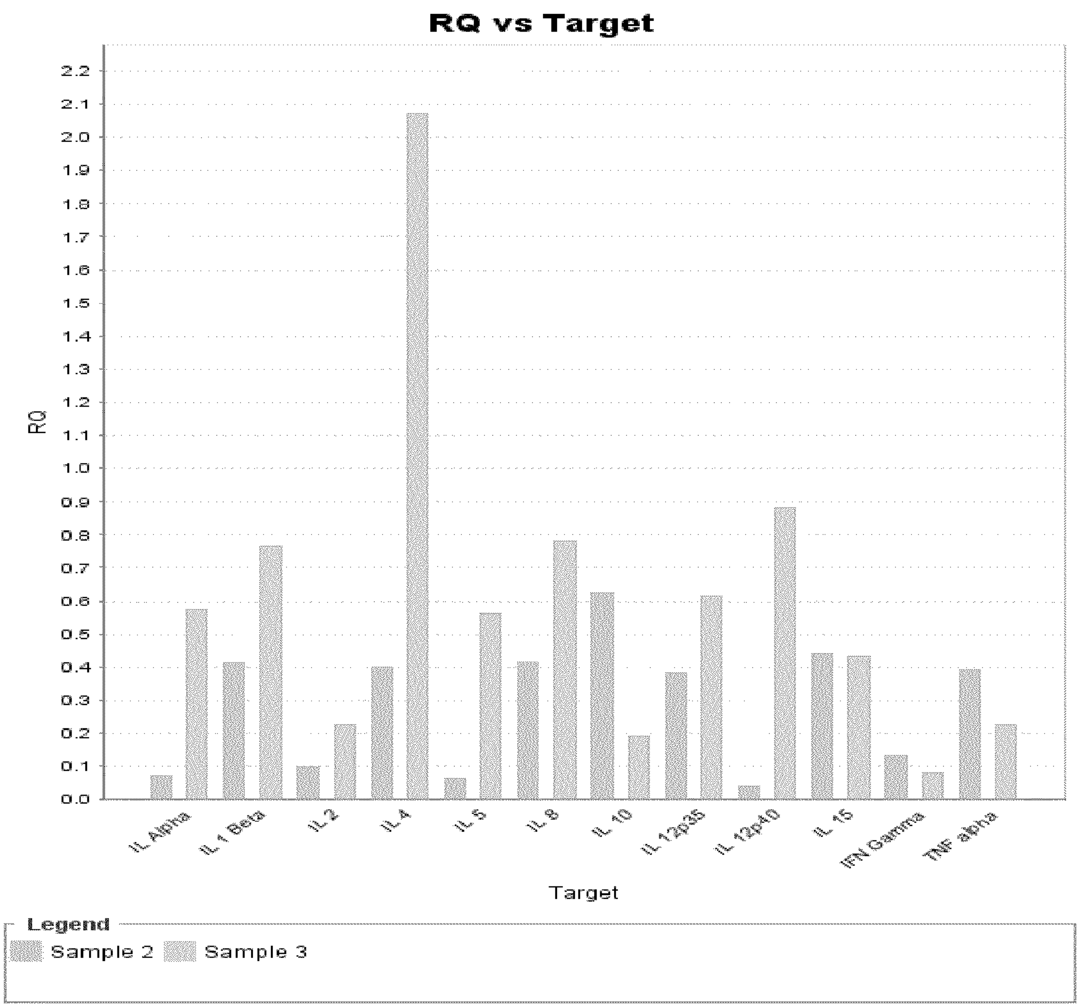
FIG. 4 graphically illustrates a cytokine gene expression study before and after oxymatrine (RQ is the gene expression ratio).
Figure 5:
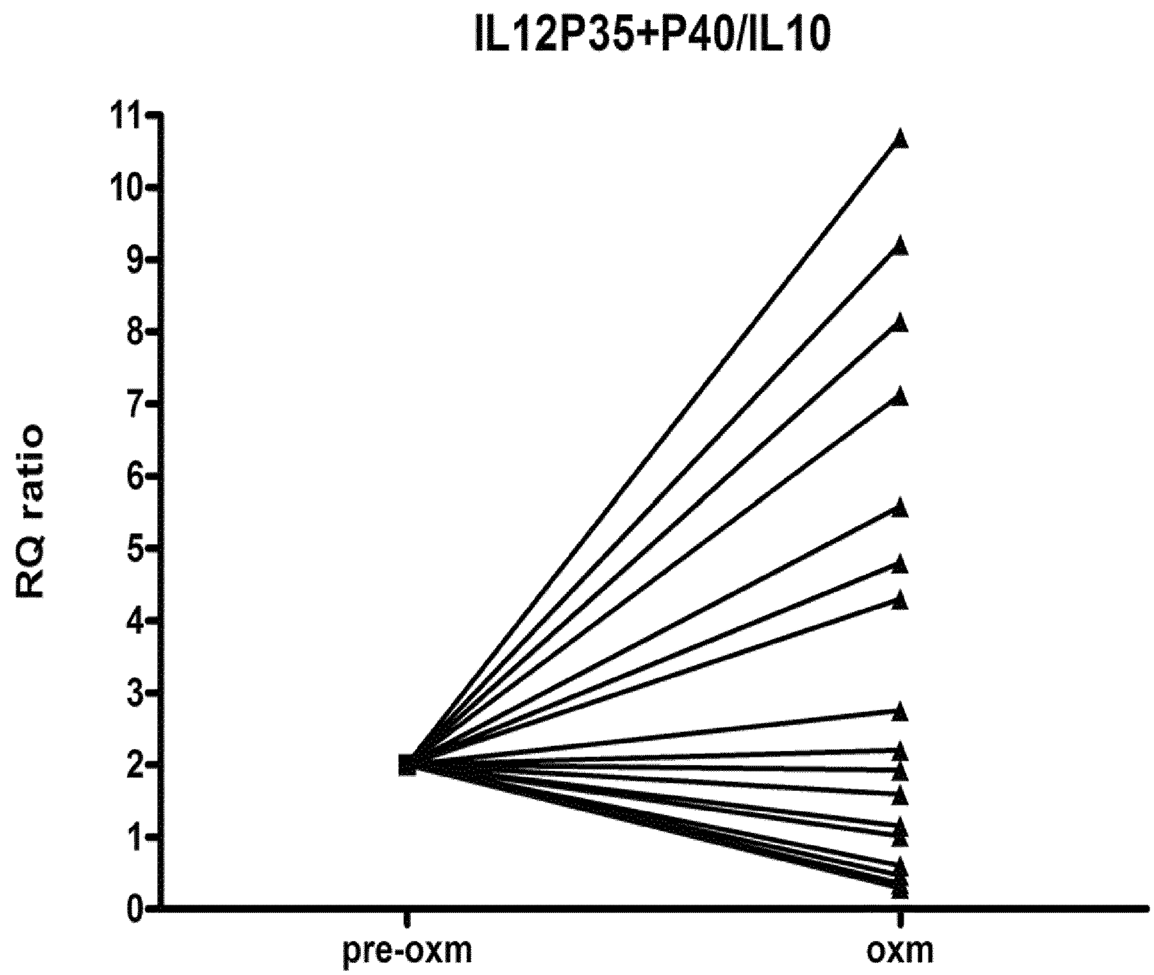
FIG. 5 graphically illustrates cytokine gene expression of interleukin-12P35+P40/interleukin-10 in tissue from CFS patients at the start of (pre-oxymatrine) and during oxymatrine therapy (n=17). Seven responders have greater than 2-fold increase of the interleukin-12P35+P40/interleukin-10 ratio whereas the ratio in ten non-responders remained the same or decreased.

A cytokine gene expression study on blood samples before (Sample 2) and after (Sample 3) taking oxymatrine for 15 months in one patient, is graphically illustrated in FIG. 4. The data showed significant increase in Th1 cytokines gene expression (interleukin-2, interleukin-12, interleukin-15) and significant decrease in regulatory Th2 cytokine gene expression (interleukin-10). FIG. 5 illustrates that neutralizing antibodies CBV 3 and CBV 4 were obtained serially over a three year period (performed by ARUP laboratory, Salt Lake City, Utah).

Example 8

Use of Oxymatrine to Treat *Mycobacterium avium* Complex Infection

A 51 year-old white female with known history of *Mycobacterium avium* complex (MAC) infection of the lung and bronchiectasis for several years was treated with clarithromycin, ethambutol, ciprofloxacin and rifabutin for about five years. As a result of persistent positive sputum culture for MAC, the patient was also treated with gamma interferon (an immune booster) without significant benefit. Intravenous amikacin was added following right middle and left lingula lobectomy. In spite of the above therapy, sputum and repeat bronchial washing obtained by bronchoscopy grew MAC within three weeks. A computed tomography scan of the chest remained unchanged except for the post-surgical changes.

Because of persistent positive cultures despite the four drug therapies, the patient was started on oxymatrine, which she tolerated well. Within two months, the night sweats decreased from twice a week to once every two weeks. Sputum became clear in color then resolved. About two months after the start of oxymatrine, the patient had fevers, flu-like symptoms, increase in non-productive cough, bilateral uveitis and elevation of liver enzymes to 3.5 times normal values. The symptoms lasted two weeks and resolved after tapering dose of oxymatrine to 200 mg bid. Liver enzymes returned to normal within six weeks. Repeat bronchial washing obtained by bronchoscopy six months after onset of oxymatrine therapy showed no growth of MAC. Repeat computed tomography scans of the chest showed healing and calcifications of the lesions. The anti-MAC medications were discontinued after eight months of oxymatrine therapy. The dose of oxymatrine was tapered to 100 mg tid at four and a half months of therapy and then stopped after six months of total therapy. The patient felt well at the six month follow-up.

Example 9

Use of Oxymatrine to Treat Chronic Recurrent Varicella-Zoster Virus (VZV) Infection (Shingles)

A 42 year-old Chinese American female developed recurrent shingles after multiple episodes of sinus infections and sinus surgeries. She also had chronic indigestion and nausea. Fatigue became so severe that she was bedridden for several years. Continuous treatment with antiviral agents for VZV did not alter the frequency and severity of VZV outbreaks.

Immunologic studies showed normal T lymphocyte counts, including CD4+ and CD8+ lymphocytes and ratios thereof. Coxsackievirus B4 antibody was 1:320. Enterovirus protein was demonstrated in the stomach biopsy by immunochemical staining. The patient was started on oxymatrine 200 mg bid. Three months after taking the oxymatrine, the patient went back to full-time work. The outbreaks of shingles were less often and not as severe.

Example 10

Figure 6:
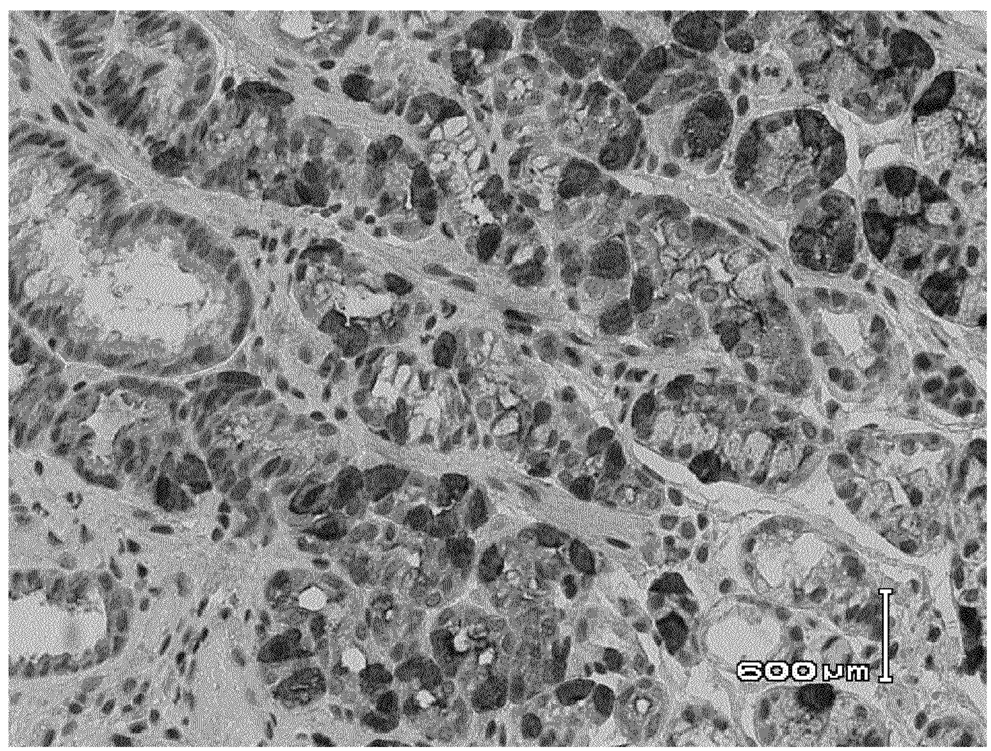
FIG. 6 illustrates an immunoperoxidase-stained stomach biopsy (case 9).

Use of Oxymatrine to Treat Acute Enterovirus Infection of the Gastrointestinal Tract A 79 year-old female developed subacute onset of severe fatigue, nausea, anorexia and progressive weight loss of 20 pounds following an upper respiratory infection. Laboratory studies showed no significant findings. An upper gastrointestinal endoscopy showed mild gastritis, which was confirmed by pathological examination of a biopsy. Immunoperoxidase staining of stomach biopsy demonstrating presence of enterovirus protein (FIG. 6) before the patient started taking oxymatrine.

Her symptoms promptly responded to 200 mg of oxymatrine bid, and she resumed her normal activity after taking oxymatrine for ten days, and her appetite improved immediately.

Example 11

Treating Diarrhea Using Oxymatrine

A 60 year-old female developed continuing watery diarrhea, as many as twenty episodes a day, and mild fatigue for three months. Laboratory studies and stool work-up were completely negative. A colonoscopy showed mild inflammation in the distal colon. Multiple biopsies showed minimal inflammation but otherwise no significant pathologic findings. An immunoperoxidase staining of the biopsies showed the presence of viral protein in the colonic epithelium. She failed Asacol therapy. The diarrhea resolved completely in a few days after starting oxymatrine 200 mg bid.

Example 12

Treating Diarrhea Using Oxymatrine

Figure 7:
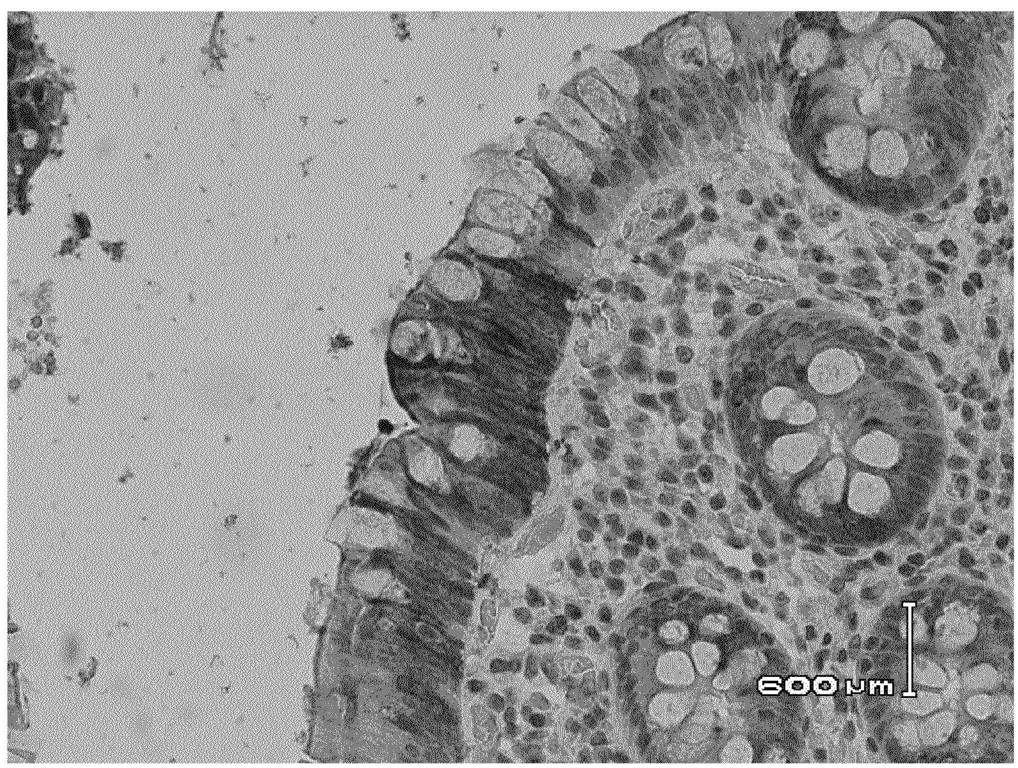
FIG. 7 illustrates an immunoperoxidase-stained stomach biopsy (case 11).

A 76 year-old white female developed severe watery diarrhea for two months. Stool evaluation was unremarkable. Colonoscopy showed minimal inflammatory changes in the colon and immunoperoxidase staining of the colon biopsy showed the presence of enterovirus protein (FIG. 7). Asacol did not help the symptoms. After starting oxymatrine, the diarrhea resolved within one week. She continued to do well for six months on the medication. A decrease of medication to half the dose cause a relapse of the symptoms, which resolved after increasing the dosage.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific example embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Example embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What I claim is:

1. A method for treating myalgic encephalomyelitis or chronic fatigue syndrome comprising:

administering to a human patient suffering from said myalgic encephalomyelitis or chronic fatigue syndrome an anti-infective amount of substantially pure oxymatrine or a pharmaceutically acceptable salt or ester thereof, wherein said anti-infective amount of said substantially pure oxymatrine is administered at least once daily in an amount between about 10 mg and about 1000 mg; and thereby treating said myalgic encephalomyelitis or said chronic fatigue syndrome.

2. The method according to claim 1 wherein said chronic infectious disease is chronic fatigue syndrome.

3. The method according to claim 1 wherein said chronic infectious disease is myalgic encephalomyelitis.

4. The method according to claim 1 wherein the substantially pure oxymatrine is administered twice daily at a dose between about 100 mg and about 500 mg per administration.

5. The method according to claim 1 wherein the substantially pure oxymatrine further includes at least one pharmaceutically acceptable excipient.

6. The method according to claim 1 wherein said method further comprises the step of diagnosing said chronic infectious disease using a gastrointestinal biopsy before said administering step.

7. The method according to claim 6 wherein said gastrointestinal biopsy is a stomach biopsy.

8. The method according to claim 6 wherein said gastrointestinal biopsy is a colon biopsy.

9. The method of claim 6, wherein said gastrointestinal biopsy is conducted to determine the presence of enterovirus in the patient.

10. The method of claim 9, wherein said gastrointestinal biopsy is a stomach biopsy.

11. The method of claim 9, wherein said gastrointestinal biopsy is a colon biopsy.

* * * * *